(12) United States Patent
Lin (10) Patent No.: US 8,708,982 B2
(45) Date of Patent: Apr. 29, 2014

(54) WOUND PROTECTION AND THERAPY SYSTEM

(76) Inventor: Edward D. Lin, Osprey, FL (US)

( * ) Notice: Subject to any disclaimer, the term of this patent is extended or adjusted under 35 U.S.C. 154(b) by 2098 days.

(21) Appl. No.: 11/122,863

(22) Filed: May 4, 2005

(65) Prior Publication Data

US 2006/0253089 A1 Nov. 9, 2006

(51) Int. Cl.
*A61M 1/00* (2006.01)

(52) U.S. Cl.
USPC .............................. 604/307; 602/41; 604/313

(58) Field of Classification Search
USPC ............. 604/23, 24, 304, 305, 307, 301, 289, 604/290, 293
See application file for complete search history.

(56) References Cited

U.S. PATENT DOCUMENTS

| | | | | |
|---|---|---|---|---|
| 4,328,799 A | * | 5/1982 | LoPiano | 604/23 |
| 5,154,697 A | * | 10/1992 | Loori | 604/23 |
| 5,667,502 A | * | 9/1997 | Holtermann | 604/342 |
| 2004/0010207 A1 | * | 1/2004 | Flaherty et al. | 600/573 |
| 2004/0153032 A1 | * | 8/2004 | Garribotto et al. | 604/131 |
| 2005/0137521 A1 | * | 6/2005 | Stenzler | 604/23 |
| 2005/0220849 A1 | * | 10/2005 | Hickey | 424/445 |
| 2006/0146234 A1 | * | 7/2006 | Bear et al. | 349/96 |

FOREIGN PATENT DOCUMENTS

| | | | | |
|---|---|---|---|---|
| EP | 1674898 A1 | * | 6/2006 | G02B 5/30 |
| GB | 288220 A | * | 7/1927 | A61M 35/00 |

* cited by examiner

*Primary Examiner* — Melanie Hand
(74) *Attorney, Agent, or Firm* — Renner Kenner Greive Bobak Taylor & Weber (57) ABSTRACT

A method and apparatus for protecting and treating wounds are provided. A housing is adapted to be adhesively secured over the wound of an injured or infected person. The housing has an opening for access to the wound, and is further provided with inlet and outlet ports for the application of therapeutic materials. There is particularly provided a program for a closed looped system for such wound care. Additionally, the invention provides for a protective and treating cover for the eye, which can be either opaque or translucent. Additionally, a mechanism for accurately depositing eye drops without risking injury to the eye is also provided.

20 Claims, 4 Drawing Sheets

WOUND PROTECTION AND THERAPY SYSTEM

TECHNICAL FIELD

This invention relates to protective dressing and cover for an injured body part, such as the eye, as well as methods and devices for simplifying general wound care, delivering medication thereupon and accelerating healing by creating an optimal microenvironment using a range of therapeutic modalities.

BACKGROUND ART

With improving medical technologies, and a growing as well as aging world population, both the number of surgical operations and their complexity increase. Take just the eye, for example, millions more elderly patients each year undergo various ophthalmic surgeries including cataract extraction, intraocular lens replacement, cosmetic blepharoplasty, entropion, ectropion and tear duct repair. Younger patients also increasingly seek LASIK correction of myopia and astigmatism. More infants also undergo strabismus or amblyopia (lazy-eye) correction. As a result, many tens of millions of eye surgeries occur each year following which the operated eye needs to be protected in the weeks following eye surgery from pressure injury and receive liquid topical medications several times daily. This is especially critical following "open globe" operations (such as cataract surgery, because accidental pressure can lead to rupture of the globe, and partial or total loss of vision). Similarly, following accidental injury to the eye (from foreign body to chemical splashes) the injured eye is typically covered and protected for a period of time with multiple daily administration of topical medication.

All of the above post-operative or post-trauma care of the eye currently requires an uncomfortable rigid metal or plastic discoid fenestrated eye shield to be taped in place over the periorbital area. The disc is ovoid in shape and measures 1 mm to 3 mm thick, depending on material. The discoid shield and the adhesive tape holding it in place must be removed multiple times each day for medication administration. The edge of the eye shield compresses uncomfortably against the bony prominences underlying the eyebrow and cheek, and the absence of a seal between the shield and the skin precludes taking a shower or simple washing of the head or face. The fenestration of the discoid shield is to diminish the amount of light coming into the photosensitive eye, or to allow the patient to see, depending on the personal circumstance of the patient.

Even more annoying, and uncomfortable to the point of pain, is the peeling back of the tape holding the eye shield to administer medication several times a day. This tedious and unpleasant process is aggravated by the discomfort of peeling adhesive tape off eyebrows and sensitive facial skin. Elderly patients are especially susceptible to the associated problems and complications because they have thin atrophic skin and brittle capillaries that bruise easily, their vision is already impaired and they often do not have skilled live-in help to assist with properly dressing the eye and administering the medication multiple times each day. This situation threatens patient compliance, and both the quality of post-operative eye care and surgical outcome. The repeated peeling of adhesive tape removes the buffering layer of dead squamous cells and brings fresh adhesive into proximate contact with microcapillaries, t-cells and histiocytes. This incites tissue irritation or allergic reaction to the tape adhesive. Lastly, the eye shield and associated tape is visually unattractive and draws unwanted attention from on-lookers.

Also difficult is the precise delivery of liquid eye medication to oneself. It is difficult to judge:

1) when the medicine dropper is positioned properly over the eye (such that the medication does not land outside of the eye margins and the expensive medication is wasted), or 2) when the tip of the eye drop dispenser is too close to the eye (which would risk contamination of the dispenser tip and risk abrasion injury to the cornea).

A variety of other eye patches are disclosed in prior teachings, most comprising of soft padded ovoid patches, some with an inflatable bladder or intermediate pocket for inserting extra padding or compress. These prior art all require changing with each medication delivery, do not protect the eye from water (as while taking a shower), and with the exception of the hard discoid shield, do not protect the injured eye against external pressure.

Turning attention now to examples of other types of wounds, this invention further pertains to 1) contaminated wounds, 2) chronic decubitus wounds and 3) wounds from plastic and reconstructive surgery.

The cornerstone to wound management is maintaining a clean, sterile and optimized environment for healing, including good oxygenation, nutrition and vascular flow. Many wounds are "dirty" from traumatic injury or from infection superimposed on underlying disease processes (such as diabetic peripheral vasculopathy, other co-morbidities or malnutrition) that renders the body incapable of dealing with the extent of tissue compromise and growing microbial load.

In a blast injury, as might be sustained by a soldier, an enormous load of soil organisms is forced deep into tissue, which then feeds and multiplies on the extensively damaged tissue. This is a very challenging category of wounds to clean and heal. Perhaps the most challenging wound of all is the chronic decubitus wound because the underlying vascularity that determines tissue viability is often substantially compromised. Wounds from plastic and reconstructive surgery may entail skin grafts or tissue pedicles that have tenuous vascularity, must be protected from outside shear force (unintended movement upon the graft tissue, such as during dressing change) and need an optimum, highly protected environment for healing.

Wound closure involves the migration of epithelial and subcutaneous tissue from the wound periphery toward the center. A good blood supply, aided by the normal activation of a variety of immune system cells is important to the healing process. However, the larger or more infected the wound is, the greater is the disruption of the original blood supply. This translates to a greater degree of local edema, microstasis, hypoxia and hypoperfusion; all increasing the likelihood of wound deterioration and infection.

Whenever the wound is not clean, wound debridement is an essential precursor to wound closure. It is the removal of necrotic tissue, exudate, and metabolic waste from a wound and improves the healing process. It reduces the bio-burden of the wound; controls and potentially prevents wound infection, especially in deteriorating wounds; and allows the physician to visualize the wound walls and base to assess viable tissue. Exudate usually results from infection. Staphylococcus aureus, for example, is known to produce a fibrin-rich biofilm that is resistant to the body's natural immune response to foreign bodies. Residual necrotic tissue not only impedes wound healing, but can also result in generalized infection, osteomyelitis, septicemia, loss of limb, or even death. Removing the necrotic tissue will help restore circulation and oxygen delivery to the wound, both critical to healing. Wounds at sites of rich blood supply, such as the scalp, heal faster and are less prone to infection. Oxygen is required for energy-dependent metabolic processes, production of free radicals that kill bacteria, and proliferation of cells, such as fibroblasts and epithelial cells, which are crucial for wound healing. Bacterial overgrowth under hypoxic conditions may compete with the healing tissue for nutrients and produce exotoxins and endotoxins that could damage newly generated and mature cells.

Hypoxic conditions in dirty wounds also encourage anaerobic bacterial growth which is serious, potentially life-threatening and difficult to treat. Hyperbaric oxygen chambers are available in certain tertiary medical centers and therapy time is limited to a few hours due to oxygen toxicity. Medical problems commonly treated with hyperbaric oxygen therapy include non-healing wounds, osteoradionecrosis, acute carbon monoxide poisoning, acute gas embolism, burns, and certain infections. Yet, medical use of hyperbaric oxygen must be applied conservatively because of the potential risk of toxicity to the central nervous system (seizure) and lungs. These problems and resource scarcity belie the enormous cost of proper wound care: $20 billion annually in the US just for chronic wound care in nursing homes. An estimated 1.2 million people with diabetes suffer from lower extremity ulcers each year, and of all the foot amputations in the United States, 84 percent, or 60,000 amputations, are related to diabetic foot ulcers. Proper and timely wound care can significantly reduce the incidence of such tragic outcome. The teachings of this invention will help curtail the costs and complications of wound care.

Debridement may also be required to prepare the wound bed prior to application of new biomaterials used to treat chronic wounds, such as cultured keratinocytes and a bioengineered human skin equivalent. As these modalities are used more extensively in clinical practice, selecting the appropriate debridement option will become more critical.

Because necrotic and devitalized tissue range from moist, yellow, green, or gray tenacious plaques to thick, leathery black eschar if the wound dehydrates, its removal can pose a challenge. In addition to posing a barrier to oxygen and nutrients, it can also serve as a breeding ground for microbes, and may mask underlying buildup of fluid or abscesses.

Several types of debridement are available. Mechanical methods include wet and dry dressings, whirlpool, and pulsed lavage. It is labor intensive, may be painful and nonselective because it does not discriminate between viable and nonviable tissue. Newly formed epithelium can also be removed by these methods.

Chemical debridement methods, including topical use of enzymatic gels and solutions can dissolve necrotic tissue from the wound. Various types of enzymes target specific components of dead tissue, such as fibrin and collagen. Enzymes that act on necrotic tissue are categorized as proteolytics, fibrinolytics, and collagenases. Enzymes for wound debridement are mostly formulated as ointments, solutions absorbed by a wet gauze, hydrocolloids, or hydrogels. The efficacy depends on the enzyme employed, with fibrinolysin ointment regarded as ineffective, collagenase ointment somewhat effective, and papain-urea ointment most effective. Because the interface or contact between the enzymatic dressing and necrotic substrate has to be manually changed and refreshed, a prolonged time is required for these treatments to deliver significant improvement. This ranges from four days to three weeks with daily wound treatments for fresh ointment supply (especially during the first week).

A laboratory study on rabbits and mice by Yaakobi et al and published in July in Wounds 16(6):201-205, 2004, reported that by continuously dripping proteolytic enzyme solutions such as bromelain, collagenase, papain, pepsin, protease and trypsin in suitable medium, they were able to vastly shorten the debridement time. The authors concluded, "The feasibility of this approach was demonstrated on lab animals by studies on skin treatment and wound debridement. Our results have clearly demonstrated technical feasibility and efficacy of streaming of enzyme solution. The time required for effective treatment was on a scale of a few hours, substantially shorter than the several days/weeks required for treatment with enzyme-containing ointments. The authors, however, gave no suggestions how to bring this laboratory finding to clinical application, and to contain the continuous enzyme solution run-off if applied at the bedside in a clinical setting.

Lastly, biological methods of wound debridement including maggots of the blowfly, *Phaenicia sericat*, and certain leeches have also been shown to be effective in debriding certain types of wounds. However, confining them within the wound site can pose a challenge and when they wander outside the wound onto adjacent normal skin, a creepy-crawly sensation is unpleasant for the patient. It is therefore also an aspect of this invention to provide methods wherein such creatures can be easily confined in a closed space and their distracting sensation upon the patient minimized.

Recent advances in general wound therapies have included the application of continuous suction to the underside of a wound dressing. It is believed that such treatment helps to reduce tissue edema, enhance drainage and fibroblast cell migration. While negative pressure appears to accomplish the above, the advanced wound chamber system disclosed herein will provide a yet more advanced system of wound care and therapy as never before available. This includes automated cycles of enzymatic debridement, wound lavage, irrigation with antimicrobials and immune modulators, optimization of microenvironment with the infusion of high-concentration oxygen, nitric oxide, cyclical application of positive and negative pressure to simulate physiologic circulation and accelerate wound healing. These methods, devices and special features will be disclosed in detail below.

SUMMARY OF THE INVENTION

Given the aforedescribed current state of the art, it is an aspect of this invention to provide an effective and yet economical device that would simplify and enhance wound treatment by means of a direct-view inspection chamber that encloses and protects a wound and maintains around it certain beneficial microenvironments that heretofore have been difficult or impossible to attain.

It is also an aspect of this invention to provide a method of wound care that would sharply reduce the attention and effort needed for wound dressing changes, and accelerate the healing schedule by enabling novel methods of therapy, delivered with ease and precision at the appropriate time.

It is another aspect of this invention to provide a method of wound care that provides for modular compartments with interchangeable and engageable parts to customize for a patient's specific needs.

It is another aspect of this invention to provide a method and device for eye care that enables accurate dispensing of eye drops into the eye It is another aspect of this invention to provide a method and device for wound care that reduces the frequency of dressing changes and reduces the incidence of tape irritation reaction and tissue maceration through the application of a layer of cyanoacrylate to the skin surrounding the wound.

It is an aspect of this invention to provide a method and device for wound care through the application of a layer of cyanoacrylate outside the immediate wound area to generally confine biological debridement agents within the wound, and discourage their migration beyond the periphery of the wound and further diminish unpleasant patient sensation associated with the agents crawling over normal skin.

It is another aspect of this invention to provide a method of wound care to enables infusion of therapeutic fluids such as oxygen, vasodilators such as nitric oxide, proteolytic enzymatic lavages or antimicrobial solutions, pro-epithelial factors and other growth or healing modulators.

It is another aspect of this invention to provide a programmable device that automatically carries out prescribed customized regimens of wound care that include beneficial infusions, lavages, heating, cooling and other therapeutic fluids such as oxygen, vasodilators such as nitric oxide, proteolytic enzymatic soaks, antimicrobial solutions, pro-epithelial growth and healing factors and modulators.

It is an aspect of this invention to provide a method/device of wound care that eliminates dressing and dressing changes, allows direct visualization and inspection of wound, relieves focal pressure on the wound and provides programmable optimized milieu for the wound through the delivery of beneficial therapies.

It is an aspect of this invention to provide a method/device of wound care that provides for cyclical application of positive pressure oxygen alternating with negative pressure to improve the circulation and drainage to the wound area.

BRIEF DESCRIPTION OF DRAWINGS

For a complete understanding of the objects, techniques and structure of the invention, reference should be made to the following detailed description and accompanying drawings wherein.

DETAILED DESCRIPTION OF PREFERRED EMBODIMENT FOR CARRYING OUT THE INVENTION

Figure 1:
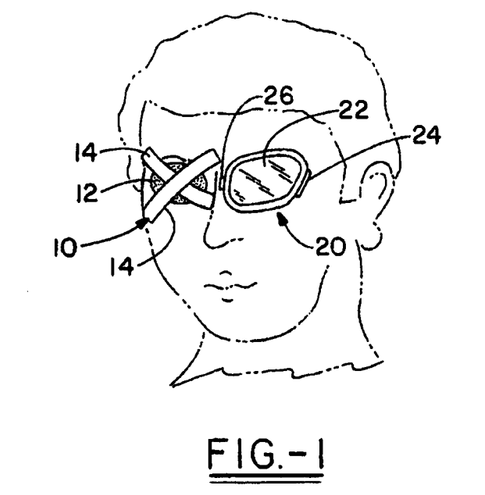
FIG. 1 shows an individual wearing the current-art compression-resistant eye dressing over his right eye compared to a compression resistant eye dressing chamber over his left eye as disclosed herein.

FIG. 1 shows an individual wearing two types of compression-resistant eye dressing. Over the right eye is the standard currently available dressing 10 comprising a rigid aluminum or plastic disc 12 with multiple fenestrations. Pieces of adhesive tape 14 are used to hold the disc in place and must be removed each time eye medication needs to be delivered, typically three to four times each day. Once the adhesive tape is pulled off, it does not stick again adequately and typically has to be replaced after each use. Over the course of a 7 to 10-day therapy period, the removal and reapplication of the tape 20 to 40 times results in considerable skin irritation and adhesive residue build-up. Furthermore, the current eye dressing does not protect the eye against wetness and does not allow the patient to shower or shampoo the hair during the course of treatment.

Over the left eye is shown one embodiment of this invention in the form of an eye dressing chamber 20. A lid or cover 22 that can be clear or of variable tint and opacity covers a form fitting conforming base ring which is adhesive mounted to enclose the entire periorbital area. The lens can open and close via locking means 26 and is attachable to the base ring via a hinge mechanism 24. Further construction detail is provided in FIGS. 5A through 7.

Figure 2:
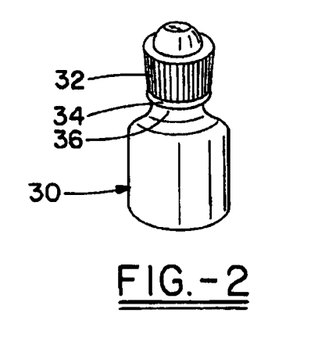
FIG. 2 is a perspective view of a typical eye dropper bottle showing a standard collar and neck.

FIG. 2 is a perspective view of a typical eye dropper bottle 30 showing a standard collar 34 and a neck 36 between the collar and bottle. A cap 32 keeps the tip of the bottle clean. Unfortunately, it is an imprecise and difficult task for a person to administer eye drops to oneself. Oftentimes, the tip is not properly centered over the eye, so the expensive medication is wasted. At other times, only a portion of the drops lands within the eye resulting in an inadequate dose. If the patient recognizes that less than the full dose is received, he may attempt to remedicate again, hoping to deliver a full drop to the eye the second time. This is not a significant problem for antimicrobial drops; however, many eye drops, especially those for the treatment of glaucoma are vasoactive and can lead to pressure drop and other untoward effects. At other times, the tip of the dropper can come too close and actually contact the eye, causing the tip and bottle content to become contaminated; worse yet, it can also cause a corneal abrasion. A simple to use device is needed to help reliably deliver medication drops to the eye.

Figure 3:
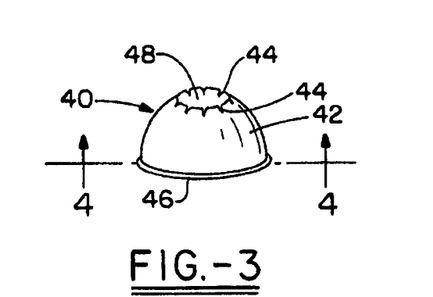
FIG. 3 is a perspective view of an eye-dropper dome designed to aid precision delivery of eye drops.

FIG. 3 is a perspective view of an eye-dropper dome 40 designed to aid precision delivery of eye drops. Its general shape substantially resembles a tall entree serving cover or truncated dome. At the wide end is a smooth and thickened lower rim 46 to prevent any scratch injury to the eye, and at the narrow end is an opening 48, sized to fit the neck 36 of eye dropper bottles. Short slits 44 emanate from opening 48 and divide the immediate perimeter area into locking tabs that yield to expansive pressure. In actual use, this dome is inserted, upside down with smaller opening first, over a capped eye-dropper bottle. The locking tabs will yield over the bottle collar 34 and lock around the neck 36 of the bottle.

Figure 4:
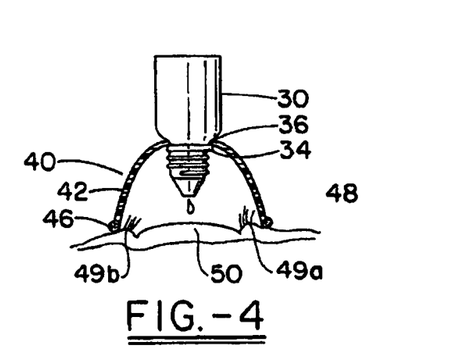
FIG. 4 is a cross sectional view of FIG. 3 taken along line 4-4 showing the shroud locked between the collar and neck of the bottle and dispensing an eye drop over the center of the eye.

FIG. 4 is a cross sectional view of FIG. 3 taken along line 4-4 showing the eye dropper dome locked between the collar and neck of an eye dropper bottle and dispensing an eye drop precisely over the pupil 50 of the eye. Note that the dome's wide opening easily encloses the upper and lower eyelashes 49a and 49b and should generally be around 25 to 30 mm in diameter. The height of the dome is such that while engaged with the neck of the bottle, the tip of the bottle will not come into contact with the eyelashes, typically 30 mm or more in height. To use the dome-equipped eye dropper bottle, the patient simply uncaps the bottle and engages the rim 46 of the dome against the bridge of the nose and the supraorbital margin, an easy-to-find bony prominence immediately below the eyebrow 48. With the patient's head fully tilted back (or with patient lying supine), this automatically positions the tip of the dropper substantially over the center of the pupil. Even allowing for individual and racial feature differences, the bottle tip will still reliably deliver the medication drops well within the eye opening, thus accomplishing the goal of dispensing eye drops to the eye.

Figure 5A:
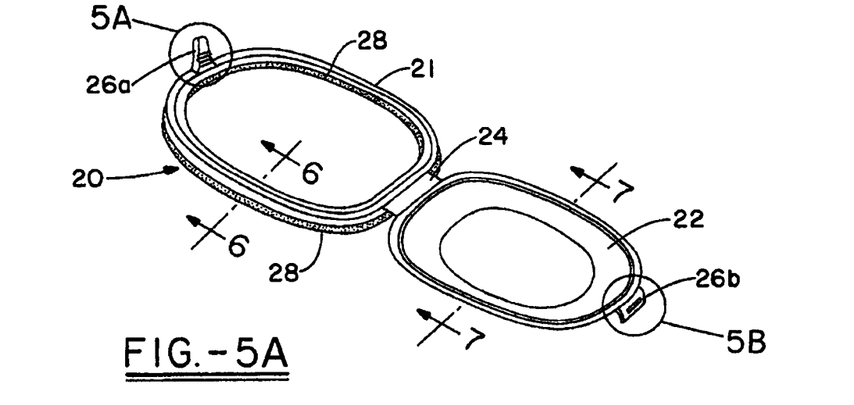
FIG. 5A is a detailed perspective view of a compression resistant eye dressing chamber showing the lid open from its base.

FIG. 5A is a detailed perspective view of a compression resistant eye dressing chamber 20 showing the cover 22 open fully from its base ring 21. The base ring is made of a flexible and conformable polymer that is moldable to fit over slight variations in facial contour. In addition to premolding the cover and base ring in mating shapes that substantially conforms to the normal contours of the periorbital region, an optional metal strip 27 (FIG. 6) can be molded within the base ring to aid in further shape adjustment and shape retention. On the underside of the base ring is a ring of suitably thick foam material 28 that further aids to cushion and seal the base ring against the periorbital contour. Beneath the foam ring is a layer of adhesive 29 for affixing the base ring and its attachments over the eye. Alternatives to using a foam ring to seal the wound chamber against the skin include the use of a miniature inflatable vinyl cushion of the type commonly found on disposable anesthesia masks. An adhesive ring affixes the cushion to the periorbital area.

Figure 5B:
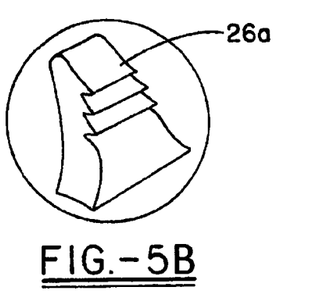
FIG. 5B is an enlarged perspective view of a ratchet locking mechanism of FIG. 5A.
Figure 5C:
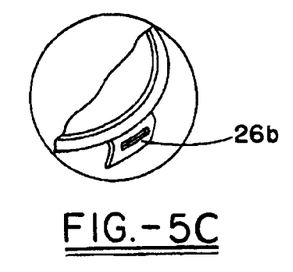
FIG. 5C is an enlarged perspective view of a locking tab mechanism of FIG. 5A.

In this illustrated embodiment, the cover 22 of the eye wound chamber is attached to the base ring via a living hinge 24 similar to the type found commonly on toothpaste caps and shampoo bottles. The hinge provides a tendency to remain in either the open or closed positions, the first tendency is useful during direct examination by the physician or for medication dispensing. The cover is secured to the base ring at the opposing end by any of a number of latching means. FIG. 5B shows the enlargement of one push-away ratchet-type locking tab mechanism 26a on the nasal side of the base ring that locks with an interlocking projection 26b on the corresponding part of the cover, as shown in FIG. 5C. So as not to distract from the main features of this invention, other interlocking and hinge mechanisms for securing the cover to the ring base are deliberately not shown; but should be apparent to those skilled in the art from this disclosure.

Figure 6:
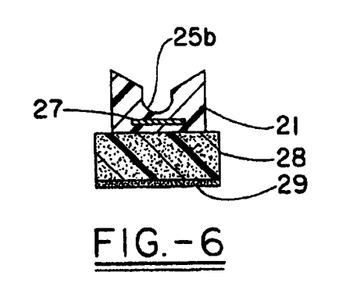
FIG. 6 is a cross sectional view of FIG. 5A taken along line 6-6 showing a polymer rim base over a foam strip with an underlying layer of adhesive.
Figure 7:
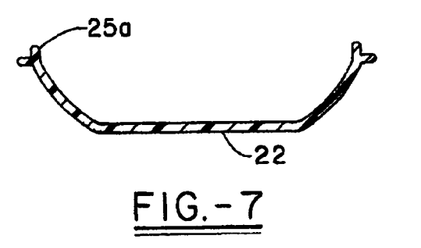
FIG. 7 is a cross sectional view of FIG. 5A taken along line 7-7 showing the dressing chamber cover with interlocking circumferential ridge.

FIGS. 6 and 7 show cross section views of FIG. 5A taken along lines 6-6 and 7-7. Surface features that aid in interlocking of the base ring 21 with the cover 22 include beveled edges leading to a center groove 25b that mate with a perimeter flange 25a. These features and other equivalents can be on the base ring or on the cover, as long as they act in concert to seal out unwanted elements such as water during a shower, or pollen and dust. Other sealing means including O-rings and compressible flanges are also evident. Detachable attaching means accommodate easy switching of the cover from clear to opaque, from ventilated to water-tight types, as may be dictated by the patient/Es changing needs. The eye wound chamber can be made in fashionable shapes and colors and can be made in tandem units like a pair of goggles and additionally be used by city dwellers to protect the eyes from smog or allergy suffers from pollen and other antigens during times of special need. Workers can also use them to protect the eyes from dust and fumes. The increasing incidence of ophthalmic allergies from biological antigens such as pollen to chemical pollutants through urbanization increases the need for a stylish and effective eye shield for everyday use When using the eye dropper dome as described in FIGS. 2 and 3 in conjunction with an eye wound chamber, the lower rim 46 of the dome can engage with the base ring or a variety of optional docking structures on the ring. One example of such a docking structure is an upper perimeter flange that projects anteriorly from the rim of the base ring; or the flange can be entirely circumferential. Such a flange can provide additional shielding from water entry, as when the patient is taking a shower.

Figure 8A:
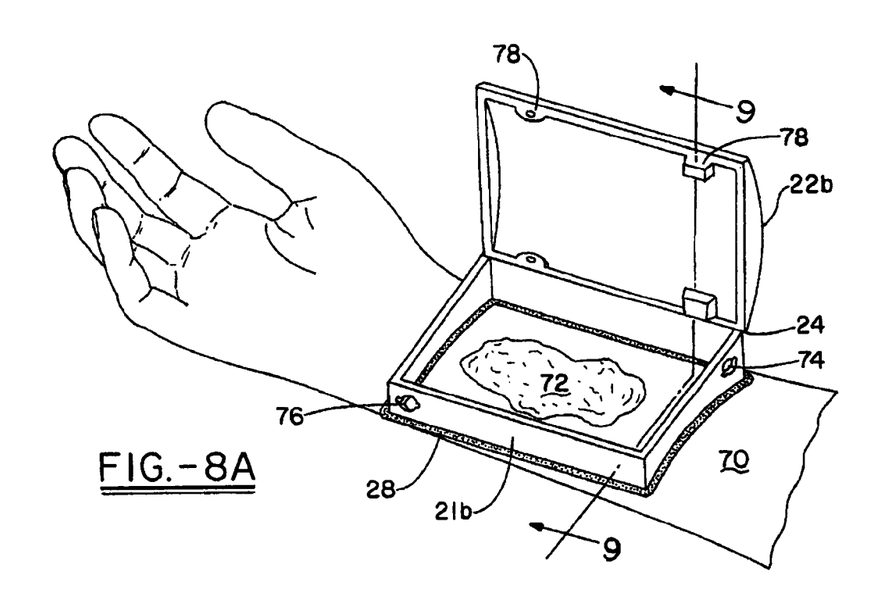
FIG. 8A is a perspective view of an advanced wound care chamber adapted to receive various fluids and medicaments.

FIG. 8A is a perspective view of a more generalized and advanced wound care chamber 70 which is shown with a modified cover 22b in open position and the lower base ring in the form of a base chamber 21b surrounding an open wound 72 of the forearm. The attachment means for this chamber to the skin can include an adhesive foam strip 28, as previously discussed, an adjustable Velcro strap with optional anchors (not shown) on the side wall of base chamber, or any one of a number of other substitutes as would be apparent to those skilled in the art.

Attachment structures such as retainer posts 78 can optionally be part of the cover 22 to allow items of benefit to be held within the chamber above the wound 72. This is further discussed under FIG. 9.

The wound chamber can additionally have an optional inlet port 74 and outlet port 76, adapted to receive infusion lines that may be uni- or bidirectional medical tubing. Again, for clarity's sake, the exact structures of these ports are not shown but any of a number of suitable medical ports and coupling mechanisms may be used and substituted. These include simple compression-fit ports, multi-way stopcocks, luerlock, and self-sealing membrane ports as commonly found in central venous catheters and other advanced vascular catheters.

Figure 11:
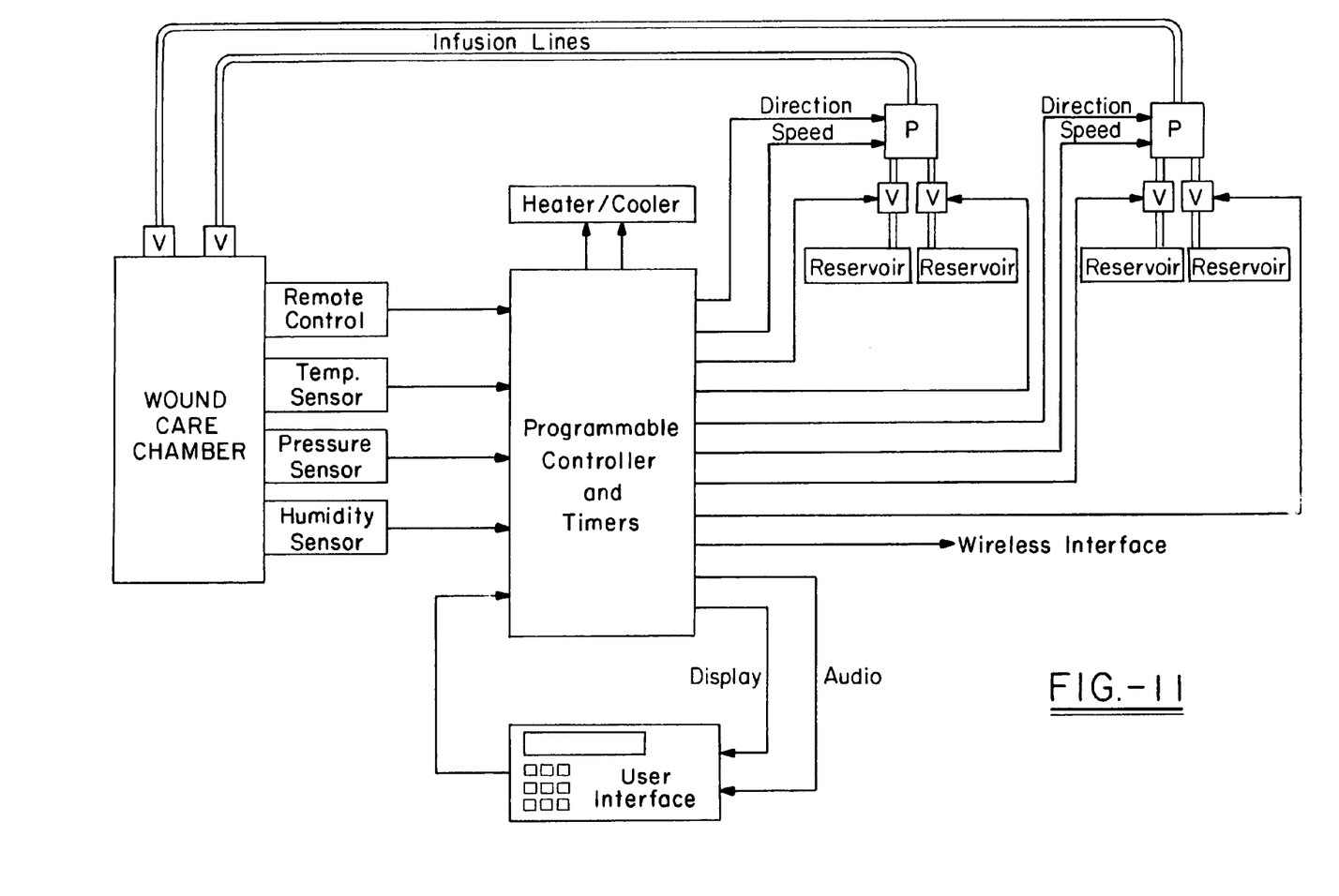
FIG. 11 is a block diagram showing an example of a particular implementation of a programmable wound therapy device designed to deliver a sophisticated regimen of therapies to optimize wound milieu and accelerate healing.

The inlet port 74 may be placed anywhere on the lid or base chamber of the wound chamber and should generally be in direct proximity to the wound. However, the drainage port 76 should ideally be in the most dependent portion of the chamber to facilitate drainage. Through the inlet and outlet ports, a circulation of chilled or heated air or oxygen may be infused depending on the nature and therapeutic needs of the wound. The air or oxygen may further be humidified. Other gases such as nitric oxide, which has vasodilator and cellular signaling properties, can also be used. Instead of needing a hyperbaric chamber, high oxygen concentration to the wound can easily be attained locally without the attendant cost and toxicity complications. All that is needed is to keep the wound chamber filled with pure oxygen, a very simple and economical task accomplished by infusing the gas from a small reservoir. Additionally, cycles of gentle or pulsatile lavage with saline or proteolytic enzymes can be passed through efficiently using a programmable pump system as shown in FIG. 11.

If the chamber 70 is to be used for therapies requiring fluid-tightness so that the fluids stay within the chamber, the foam should be of the closed-cell type. The term "fluid-tight" or related terms as used in this specification means sufficiently leak-resistant to allow insufflation or vacuum suction to create an intra-chamber pressure that is above or below ambient pressure, or to substantially retain fluids within. Various cyclical patterns of fluid application can be programmed to optimize the wound chamber milieu selected from the following:

1) Application of a local anesthetic
2) Application of a saline lavage with the effluent collected for centrifuge, cytoanalysis, microbial culture, etc.
3) If wound is contaminated with cellular and/or microbial debris, infusion of proteolytic enzymes such as papain, trypsin, collagenase, *Bacillus subtilis* protease, vibriolysin, krill protease, chymotrypsin, clastase, dipase, proteinase K, and *Clostridium* multifunctional protease
4) Application of an antimicrobial
5) Application of wound healing factors and immune modulators
6) Application of oxygen at ambient or above-ambient pressure
7) Application of nitric oxide
8) Application of low suction.

After a dirty wound is cleaned, there is no longer a need to apply lavage and proteolytic digestion cycles. At this point, the therapy focuses on delivery of oxygen and other beneficial fluids and the application of a cycle of intermittent positive and negative pressures, lasting one to several minutes per cycle. This simulates the normal vascular flow of the circulatory system at the tissue level.

When positive pressure is applied in the form of pure oxygen, oxygen is driven into the tissue and capillaries along a favorable gradient and the interstitial pressure rises pushing cellular edema into lymphatic channels to decrease the local swelling. Next, the programmable pump system reverses the pressure gradient to slightly negative, creating suction that brings fresh blood flow, along with all the inherent beneficial factors to the wound. This cycle is repeated, with cycles of other beneficial therapies such as nitric oxide, interposed. For cost saving and portable module size considerations, it may be desirable to filter effluent gases such as oxygen and nitric oxide and recycle their use. In such an arrangement, after several cycles, the gases could be completely purged and new aliquots of gases introduced.

Figures 8B, 8C, 9:
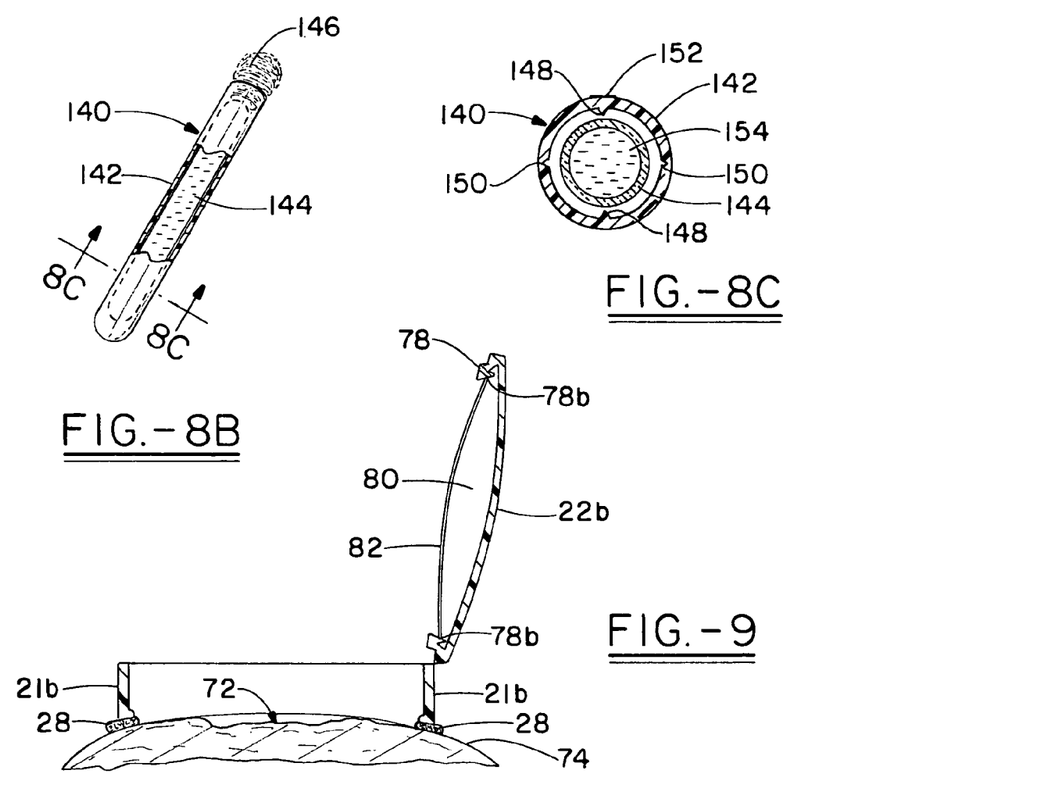
FIG. 8B is a partial sectional view of an ampoule employed in exercise of the invention.
FIG. 8C is a cross sectional view of the ampoule of the invention as shown in FIG. 8B, taken along the line 8C-8C.
FIG. 9 is a cross sectional view of FIG. 8A taken along the line 9-9 showing one adaptation of the cover to retain intra-chamber adjunct therapies such as a warm compress.

FIG. 9 is a cross-section view of FIG. 8A taken along lines 9-9. This drawing shows the base chamber 21b resting on a ring of foam base 28 that is adhesively attached to the skin 74 of the wrist. Cover 22b is shown with a convex contour and retainer posts 78 that allow simple anchoring of a retainer structure 82 such as a sheet or strip 82. Retainer sheet or strip can have perforations (not shown) which snap over or interlock with retainer pins 78b that protrude superiorly from the retainer posts. Another reverse type of anchoring is shown on the left side in the cover 22b of FIG. 8A. Many other equivalents and alternative anchoring methods are well known in the art. The retainer sheet or strip can be made of polymer or fabric. Between retainer sheet and cover 22 is created a space 80 which can retain a therapeutic item such as a heating or cooling gel pack, or other treatment modalities including moxa or moxibustion material, oxygen generator or nitric oxide donor substances.

The cover element 22 can be interchangeably attached to the base via a detachable hinge or any of a number of disconnectable engagement means that are apparent to those skilled in the arts Turning attention now back to FIG. 8, it is anticipated that under certain conditions of therapy wherein the skin surrounding a wound is exposed to prolonged periods or cycles of lavage and enzymatic therapy, maceration of the otherwise uninjured tissue can occur. Furthermore, in wound therapy using maggots and leeches, it is disturbing to the patient to have the creatures crawl beyond the wound boundaries. It is therefore an object of this invention to provide a novel method by which a durable barrier is provided against liquid penetration and wandering leeches and maggots. The method and device are hereby disclosed. As shown in FIGS. 8A and 8B, an ampoule applicator 140 has a flexible and protectable cylinder 142 of a suitable plastic or polymeric material that receives a crushable ampoule 144 having cyanoacrylate polymer contained therein. One end of the applicator 140 has a sponge applicator pad 146. Prior to the application of the wound chamber to the skin, the cyanoacrylate ampoule 142 is crushed, releasing the liquid to the sponge pad 146. The crushing of the ampoule is facilitated by sharp protruding ribs 148 interiorly of the cylinder 142. Longitudinal V-shaped grooves 150 facilitate collapsing of the cylinder 152 upon the ampoule 144 to effect the breakage and release of the liquid 154, therein. A pod 152 upon the outer surface of the cylinder 152, and in alignment with the ribs 148 directs the proper positioning for the application of crushing force and placement of the user's thumb or finger.

The applicator pad 146 is used as a paint brush to apply a layer of cyanoacrylate over all of the surface area that would be covered by the footprint of the wound chamber except for the wound itself. This layer of cyanoacrylate now provides multiple benefits including:

1) enabling the chamber base to adhere stronger and better;
2) minimize incidence of adhesive sensitivity by providing a durable barrier;
3) protect skin from maceration secondary to prolonged contact with liquids;
4) discouraging the unwanted migration of maggots and leeches via a chemical mat; and
5) dull the disturbing proprioceptive sensations patients experience when the above creatures wander outside of the wound.

An alternative method to preventing skin maceration includes the application of a polymer film that attaches to the skin via adhesive on the underside. The disadvantage of this method is that wound shapes are typically irregular, so the polymer has to be cut or trimmed to fit around the wound edge. In contrast, the novel method described using cyanoacrylate requires only a few seconds of fast painting with a sponge applicator.

Figure 10:
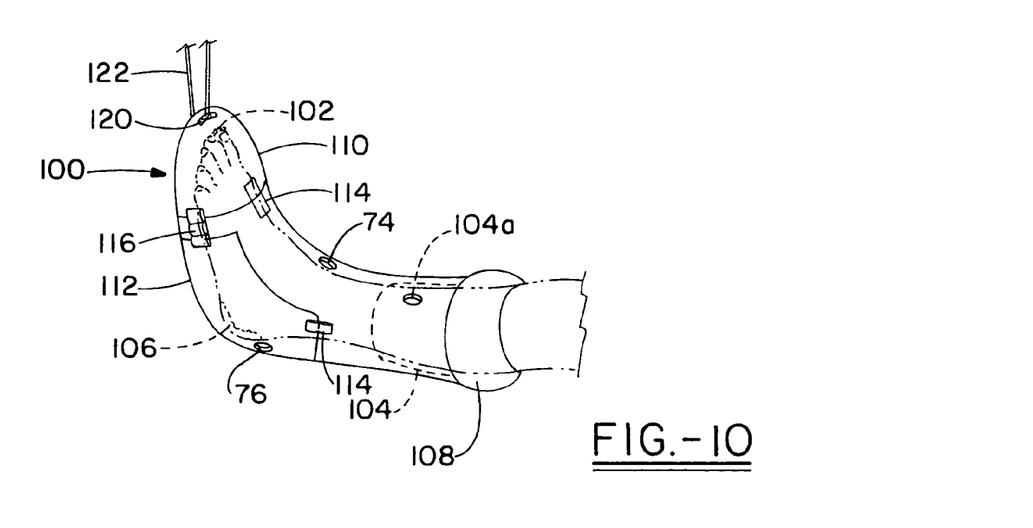
FIG. 10 is a perspective diagram showing yet another embodiment of the wound chamber system as it applies to treating decubiti of the foot.

FIG. 10 shows yet another embodiment of the wound care chamber in the form of a wound boot 100. Diabetic decubitus ulcers affecting the toe at 102 and the heel at 106 are shown. In this instance it is imperative to improve the wound milieu by taking the pressure off the ulcers and immediately instituting an aggressive program of debridement with enzymatic digestion, vasodilation and high oxygenation. A low-pressure cuff 108 has a wide pressure-diffusing inside-cuff 104 extending all the way towards the ankle. This is to diffuse the pressure to the calf and not further compromise the diminished circulation in a diabetic limb. An inflation port 104a may be optionally equipped with a pressure gauge to indicate safe pressure range near or below diastolic. The cuff can optionally be intermittently deflated and inflated via controlled mechanical means such as a timer controlled valve interposed between an air pressure source and the cuff. Alternatives to the low-pressure air cushion include high quality foam padding Wound boot 100 is shown with two openable hatches, a front hatch 110 to access the toes, and a posterior hatch 112 to access the heel. These hatches are reversibly attachable to the main boot via single action latches 114 or dual action latches 116 that have mechanisms similar to those commonly found on ski-boots and tool boxes. Many other attaching and latching means are available and will not be elaborated. One or more anchoring means 120 such as the loop shown at the toe end, allows the boot to be suspended via ropes 122 for elevation either to improve drainage or for medical examination. Infusion inlets 74 and outlets 76 are positioned to allow optimal fluid flow and drainage. Depending on the desired application, the boot may need to be of a much thicker construction than the wound chamber of FIG. 8A, and may need reinforcement ribs at appropriate areas. These considerations, modifications, substitutions, etc. would readily be apparent to one skilled in the art.

It should be apparent that similar designs can be made to accommodate and contour to other pressure areas such as the elbow or buttocks, or to accommodate frequent surgical sites such as the breast. It would be apparent to those skilled in the art that such chambers should generally be of lowest feasible profile, be pressure diffusing and provide secure anchoring means. Where the wound chamber can provide a source of contact pressure to adjacent tissue such as the contralateral leg, such pressure can be reduced by placing a soft sponge sock or other padding over the general area of contact.

FIG. 11 is a block diagram which shows an example of a particular implementation of an automated wound chamber therapy system. Some components shown, such as remote control, may be optional. Although two pumps are shown, more or fewer pumps may be used and which may be unidirectional or bidirectional. One or more pumps may have special pumping capabilities including pulsatile infusion for lavage.

Audio capabilities include alarms and speech synthesis. Alarms include reservoir low/empty alarm, pressure and temperature malfunction alarm, time elapsed alarm, etc. which may be wirelessly transmitted to caretaker as an alert. Temperature sensor includes means for heating or cooling the chamber or fluids delivered therein.

This block diagram is to illustrate an example only. The actual implementation may vary and would be readily apparent to those skilled in the art.

What is claimed is:

1. A device for protecting and treating a wound, comprising:
    a housing defining a chamber;
    a lid integral to said housing and having an interlocking or hinge mechanism for opening and closing a first portion of said housing and movable between open and closed positions to allow ready access to said chamber;
    a cushion secured about a perimeter of a second portion of said housing, said second portion being open and said cushion defining an annulus, said cushion being an inflatable air cushion or a closed cell foam cushion; and
    an adhesive layer for securing said cushion and attached housing over the body of a patient, wherein said device is fluid tight.

2. The device as recited in claim 1, wherein said cushion is pliable, conformable and compressible.

3. The device as recited in claim 2, wherein said lid is tinted to exclude light and photostimulation.

4. The device as recited in claim 2, wherein said lid or housing includes a receptacle to receive a therapeutic modality.

5. The device as recited in claim 4, wherein said therapeutic modality is selected from the group of biotherapeutic agents, moist packs, dry packs, heating packs, cooling packs, a source of oxygen, a source of nitric oxide, and moxibustion.

6. The device as recited in claim 2, wherein said housing and lid define a chamber over a wound when said lid is closed, said device with said lid closed having at least one port for passage of a therapeutic modality into or out of the chamber.

7. The device as recited in claim 1, wherein said housing forms part of a system for optimally protecting and flexibly controlling the therapeutic environment over a wound, is sustainably anchored over the wound, and has delivered within its chamber whatever beneficial therapies needed, including but not limited to proteolytic enzymes, antimicrobial lavages, biotherapy, cyclical hyperbaric oxygen, cyclical controlled suction, nitric oxide, bioengineered healing factors and substrates, and controlled humidity and temperature.

8. The device as recited in claim 7, wherein an anchoring means comprises a layer of cyanoacrylate adhesive interposed between said cushion and the skin and covers an area sized to correspond substantially to a foot print of the housing, and said layer of cyanoacrylate serves to buffer and protect the normal skin peripheral to the wound from prolonged contact with certain therapeutics and skin sensitivities.

9. The device as recited in claim 7, wherein said housing is secured over the wound by a layer of cyanoacrylate adhesive between said housing and skin surface.

10. The device as recited in claim 9, wherein said layer of cyanoacrylate adhesive is maintained in an applicator and said adhesive is applied upon discharge of the cyanoacrylate.

11. The device as recited in claim 10, wherein said applicator comprises an ampoule containing therein said adhesive to be dispensed.

12. A device for protecting and treating a wound of a patient, comprising:
    a housing defining a chamber and contacting a skin surface of the patient surrounding a wound;
    a lid integral to said housing for opening and closing a first portion of said housing and movable between open and closed positions to allow ready access to said chamber; and
    a cushion secured about a perimeter of a second portion of said housing, said second portion being open and said cushion defining an annulus
        wherein said housing forms part of a system for optimally protecting and flexibly controlling the therapeutic environment over a wound, is sustainably anchored over the wound, is secured over the wound by a cyanoacrylate adhesive between said cushion and the skin surface surrounding the wound and has delivered within its chamber whatever beneficial therapies needed, including but not limited to proteolytic enzymes, antimicrobial lavages, biotherapy, cyclical hyperbaric oxygen, cyclical controlled suction, nitric oxide, bioengineered healing factors and substrates, and controlled humidity and temperature, wherein said cyanoacrylate adhesive is maintained in an applicator and is applied upon discharge of the cyanoacrylate adhesive from the applicator, wherein said applicator comprises an ampoule containing said cyanoacrylate adhesive to be dispensed, and wherein said ampoule is maintained in an applicator cylinder having at least one sharp rib or spline extending diametrically inwardly toward said ampoule, said rib or spline facilitating breaking of the ampoule upon crushing of the cylinder.

13. The device as recited in claim 12, wherein said ampoule is maintained in the applicator cylinder having diametrically opposed relief grooves extending axially along an inner surface thereof, said grooves facilitating crushing of said cylinder.

14. A device for protecting and treating a wound of a patient, comprising:
- a housing defining a chamber and contacting a skin surface of the patient surrounding a wound;
- a lid integral to said housing for opening and closing a first portion of said housing and movable between open and closed positions to allow ready access to said chamber; and
- a cushion secured about a perimeter of a second portion of said housing, said second portion being open and said cushion defining an annulus
- wherein said housing forms part of a system for optimally protecting and flexibly controlling the therapeutic environment over a wound, is sustainably anchored over the wound, and has delivered within its chamber whatever beneficial therapies are needed, including but not limited to proteolytic enzymes, antimicrobial lavages, biotherapy, cyclical hyperbaric oxygen, cyclical controlled suction, nitric oxide, bioengineered healing factors and substrates, and controlled humidity and temperature, wherein delivery of therapeutics is via a programmable device, and wherein said programmable device has an evacuation cartridge for removal of one or more contents of said housing.

15. The devices as recited in claim 14 wherein said programmable device has a delivery cartridge for selective passage of at least one therapeutic to said housing.

16. The device as recited in claim 15, wherein said delivery cartridge couples with at least one therapeutic source for controlled passage between said housing and programmable device.

17. The device as recited in claim 14, wherein the evacuation cartridge includes means for selective collection of at least one sample for analysis.

18. A device for protecting and treating a wound of a patient, comprising:
- a housing defining a chamber and contacting a skin surface of the patient surrounding a wound, and has at least one port for variable engagement with sensors, stopcocks and connector tubings and for the passage of therapeutics; and
- a lid integral to said housing for opening and closing a first portion of said housing and movable between open and closed positions to allow ready access to said chamber; and
- a cushion secured about a perimeter of a second portion of said housing, said second portion being open and said cushion defining an annulus
- wherein said housing forms part of a system for optimally protecting and flexibly controlling the therapeutic environment over a wound, is sustainably anchored over the wound, and has delivered within its chamber whatever beneficial therapies are needed, including but not limited to proteolytic enzymes, antimicrobial lavages, biotherapy, cyclical hyperbaric oxygen, cyclical controlled suction, nitric oxide, bioengineered healing factors and substrates, and controlled humidity and temperature, wherein said sensors include monitoring and maintaining parameters selected from a group including pressure, temperature, time, humidity, and levels of hematogenous factors, enzyme, therapeutic agent, microbe, and other physiological measurements.

19. The device as recited in claim 1, wherein said housing serves as a chamber for topical treatment using nitric oxide to enhance vasodilation and blood flow to the wound area.

20. The device as recited in claim 19, wherein said housing serves as a chamber for topical treatment using nitric oxide under pressure, wherein the pressure drives the nitric oxide deeper into wound tissue of the patient.

* * * * *